United States Patent [19]

Deem et al.

[11] 4,101,586

[45] Jul. 18, 1978

[54] ALDOL REACTIONS WITH BIFUNCTIONAL CO-CATALYSTS

[75] Inventors: Mary Lease Deem, Bernardsville; Kenneth Charles Stueben, Bridgewater, both of N.J.

[73] Assignee: Union Carbide Corporation, New York, N.Y.

[21] Appl. No.: 679,715

[22] Filed: Apr. 23, 1976

[51] Int. Cl.$^2$ .................. C07C 45/08; C07C 49/04
[52] U.S. Cl. ...................... 260/593 R; 260/601 R; 260/586 C
[58] Field of Search ............... 260/601 R, 602, 586 C, 260/593 R

[56] References Cited

U.S. PATENT DOCUMENTS

| 2,684,385 | 7/1954 | Biribauer et al. | 260/601 |
| 3,077,500 | 2/1963 | Heinz et al. | 260/602 |

Primary Examiner—James O. Thomas, Jr.
Assistant Examiner—Werren B. Lone
Attorney, Agent, or Firm—Bernard Francis Crowe

[57] ABSTRACT

Reaction rates of the base-catalyzed aldol reactions are enhanced by employing co-catalysts containing imidazolyl and carboxyl functionalities.

9 Claims, No Drawings

ALDOL REACTIONS WITH BIFUNCTIONAL CO-CATALYSTS

BACKGROUND OF THE INVENTION

This invention relates to base-catalyzed aldol reactions and more particularly to the use of bifunctional co-catalysts containing imidazolyl and carboxyl groups.

Organic carbonyl compounds have been converted by base-catalyzed aldol reactions into many useful products on a commercial scale. Insect repellents, solvents, plasticizers, detergents, medicaments and the like have been prepared from aldehydes, ketones and mixtures thereof. Some specific examples include 2-ethyl-1, 3-hexanediol, 2-ethylhexanol-1, diacetone alcohol, isophorone, methyl isoamyl ketone, methyl isobutyl ketone, Miltown ® and the like.

In order to improve the manufacturing economics of these products it is desirable to direct the reactions involved towards specific end products and minimize the formation of by-products. It is also desirable to increase the reaction rates of these reactions.

SUMMARY OF THE INVENTION

It has now been found that in the base-catalyzed aldol reaction of organic carbonyl compounds side reactions can be decreased and rates of formation of the planned end products can be increased by using a bifunctional co-catalyst which contains both imidazolyl and carboxyl functionalities at a molar concentration of at least about $10^{-4}$ based on the amount of the total organic reactants.

The organic carbonyl compounds of this invention include saturated and unsaturated aliphatic aldehydes having 1 to about 18 carbon atoms, such as, formaldehyde (in combination with other carbonyl compounds), acetaldehyde, propionaldehyde, n-butyraldehyde, isobutyraldehyde, valeraldehyde, isovaleraldehyde, hexanal, decanal, octadecanal, acrolein, crotonal, 2-ethylcrotonal, and the like; as well as saturated and unsaturated ketones having 3 to about 22 carbon atoms, as for example, acetone, methyl ethyl ketone, dibutylketones, methyl isobutyl ketone, methyl isoamyl ketone, mesityl oxide, 2-methylnon-5-en-4-one, and the like. The above-enumerated organic carbonyl compounds can be used alone or in mixed aldol reactions.

The term bifunctional catalysts used in this invention includes various unimolecular organic compounds. These compounds possess two different sites-a basic one (such as an N-containing heterocycle or a cyano group) and another moiety which, in the basic medium of the aldol reaction, bears a negative change (such as, a carboxylic, sulfonate, phosphate, or phenolate group). Another feature of these bifunctional cocatalysts is the presence in their structure of a long hydrocarbon or substituted hydrocarbon chain (such as an assembly of two to polymeric amounts of methylene or substituted methylene units). Most preferred bifunctional co-catalysts contain chemically linked imidazolyl and carboxylate moieties at a concentration of at least about $10^{-4}$ mole in moiety units per mole of the total organic reactants. It is to be emphasized that the bifunctional centers of these co-catalysts are not dissociated but that they are chemically linked moieties. The most preferred bifunctional co-catalysts also possess hydrocarbon chains of 4 to 18 and more methylene units.

A preferred class of bifunctional catalysts can be prepared by the acylation of the α-amino group of histidine

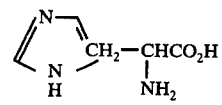

to provide $N^\alpha$-acyl histidines having 2 to 18 carbon atoms in the acyl group. A particularly preferred example is $N^\alpha$-stearoylhistidine. Other acyl derivatives of histidine include: $N^\alpha$-acetylhistidine, $N^\alpha$-octanoylhistidine, $N^\alpha$-decanoylhistidine, $N^\alpha$-decanoylhistidine, and the like.

Another preferred class of bifunctional co-catalysts can be prepared by copolymerizing 4-vinylimidazole with an α, β-ethylenically unsaturated carboxylic acid, as for example, acrylic, methacrylic, crotonic, maleic, or fumaric acids. The degree of polymerization of these copolymers is not narrowly critical and can range from oligomers to high polymers. 4-Vinylimidazole is commercially available and its copolymerization has been described by C. G. Overberger et al., [J. Amer. Chem. Soc., 85, 951 (1965)].

While the lower effective molar concentration of co-catalyst is about $10^{-4}$M, it is preferred to use a molar concentration of about $10^{-3}$. There is no upper limit but for practical purposes this value is about $10^{-2}$, unless a heterogeneous catalyst is used.

The base used as catalyst is not narrowly critical. This term includes the bases commonly used in the prior art, for the aldol condensation reaction. Alkali metal bases such as NaOH, KOH, LiOH, and the like are commonly used. However, one also can use such bases as amines (including piperidine and pyridine), metallic alkoxides (such as sodium ethoxides), metallic carboxylates (including sodium acetate), and salts of other acids (including potassium cyanide, sodium carbonate, and sodium phosphate).

The co-catalyst system disclosed herein is effective in aqueous or aqueous/organic systems as either a soluble, partially solubilized, or insoluble co-catalyst. No additional organic solvent is required for use in these aldol reactions. However, if desired, one will employ organic hydrocarbons having five to twelve or more atoms such as pentane, hexane, decane, and the like.

Temperatures above the freezing point of water to in excess of 125° C. have been used for base-catalyzed aldol condensations.

The invention is further described in the examples which follow. All parts and percentages are by weight unless otherwise specified.

EXAMPLE 1

ALDOL CONDENSATION OF N-BUTYRALDEHYDE

The 4-vinylimidazole/acrylic acid copolymer used below was prepared by the heating 5.00 g. of freshly distilled acrylic acid and 0.50 g. of 4-vinylimidazole (purchased from Haven Chemical Co.) with 0.0202 g. of azobisisobutyronitrile at 72°–74° C. for 15 minutes in a heavy-walled tube purged free of air. The polymer was dissolved in 170 ml. 2.98% ammonium hydroxide. This solution was acidified with 6N hydrochloric acid. The resultant solution was dialyzed in deionized water over 6 to 7 days, and it then was lyophilized. Analysis of the dried polymer was as follows: C, 40.13%; H, 7.54%; N, 10.82%. The intrinsic viscosity is about 1.2 (measured in ethanol:water::0.285:0.715 buffered to a pH of 7). the calculated imidazole content wa 0.36 mole/100 g. of copolymer.

Twenty-four ml. of 1.5% aqueous sodium hydroxide was placed in a 25 ml. round-bottomed flask containing a magnetic stir bar. Then 0.353g. (2.65 $\times 10^{-3}$ mole based on the imidazolyl content) of the copolymer above was added and a serum stopper was wired onto the reaction flask. The mixture was purged at room temperature with nitrogen for about 5 minutes and it then was equilibrated for about 15 minutes in a water bath maintained at 30° C. (±0.5° C.). Freshly distilled n-butyraldehyde (0.400 ml.; 0.189 mole) was injected. Following reaction for 5 minutes, the mixture was poured into 24 ml. of glacial acetic acid. The quenched mixture was analyzed in a Hewlett-Packard 5710A gas chromatograph equipped with a flame ionization detector and a Hewlett-Packard model 3373B integrator. The column consisted of 1.8 in. $\times$ 2 meter stainless steel tube packed with 10% Carbowax 20 M (trademark of Union Carbide for polyethylene oxide having an average molecular of about 19,000) on 40-60 Chromosorb T (trademark of Johns-Manville for polytetrafluoroethylene). Analysis showed 19% unreacted n-butyraldehyde and 81% 2-ethylhex-2-enal.

A Control (A) was run following the procedure of Example 1 with the exception that no 4-vinylimidazole/acrylic copolymer was present. The product contained only 64% 2-ethylhex-2-enal.

EXAMPLE 2

ALDOL CONDENSATION OF N-BUTYRALDEHYDE

The procedure described in Example 1 was followed using 0.0054 g. of $N^\alpha$-stearoylhistidine (1.25 $\times$ 10$^{-4}$ mole in water). Analysis by gas chromatography indicated that more than 79% of the starting n-butyraldehyde was converted to 2-ethylhex-2-enal.

The necessity of having a bifunctional co-catalyst containing a carboxyl group as well as an imidazoyl group was shown in Control B where Example 2 was repeated with the exception that L-histidine methyl ester (2.5 $\times$ 10$^{-3}$ mole) was substituted for $N^\alpha$-stearoylhistidine. The conversion of n-butyraldehyde to 2-ethylhex-2-enal was only 64%.

Although the invention has been described in its preferred forms with a certain degree of particularity, it is understood that the present disclosure of the preferred forms has been made only by way of example and that numerous changes may be resorted to without departing from the spirit and scope of the invention.

What is claimed is:

1. In the method of converting organic carbonyl compounds selected from the group consisting of aliphatic aldehydes having 1 to about 18 carbon atoms and ketones having from 3 to about 22 carbon atoms to condensation products by a base catalyzed aldol reaction, the improvement which comprises incorporating into the reaction mixture a bifunctional cocatalyst containing both imidazolyl and carboxyl functionalities selected from the group consisting of $N^\alpha$-acyl substituted histidines and copolymers of a 4-vinylimidazole and an $\alpha, \beta$-ethylenically unsaturated carboxylic acid having 3 to about 6 carbon atoms, at a molar concentration of at least about $10^{-4}$ based on the total amount of organic reactants whereby aldol condensation products of said organic carbonyl compounds are produced.

2. Method claimed in claim 1 wherein the co-catalyst is an $N^\alpha$-acyl substituted histidine wherein the acyl group has 2 to 18 carbon atoms.

3. Method claimed in claim 2 wherein the $N^\alpha$-acyl substituted histidine is $N^\alpha$-stearoylhistidine.

4. Method claimed in claim 1 wherein the cocatalyst is a copolymer of a 4-vinylimidazole and an $\alpha, \beta$-ethylenically unsaturated carboxylic acid having 3 to about 6 carbon atoms.

5. Method claimed in claim 4 wherein the $\alpha, \beta$-ethylenically unsaturated carboxlyic acid is acrylic acid.

6. Method claimed in claim 4 wherein the $\alpha, \beta$-ethylenically unsaturated carboxylic acid is methacrylic acid.

7. Method claimed in claim 1 wherein the organic carbonyl compounds are aldehydes.

8. Method claimed in claim 1 wherein the organic carbonyl compounds are ketones.

9. Method claimed in claim 1 wherein the organic compounds consist of an aldehyde plus a ketone.

* * * * *